US011919852B2

(12) United States Patent
Tuat Pham et al.

(10) Patent No.: US 11,919,852 B2
(45) Date of Patent: Mar. 5, 2024

(54) PROCESS AND PLANT FOR SEPARATION OF A HYDROCARBON MIXTURE

(71) Applicant: LINDE GmbH, Pullach (DE)

(72) Inventors: Duc Tuat Pham, Penzberg (DE); Benedikt Kurz, Munich (DE)

(73) Assignee: LINDE GmbH, Pullach (DE)

( * ) Notice: Subject to any disclaimer, the term of this patent is extended or adjusted under 35 U.S.C. 154(b) by 821 days.

(21) Appl. No.: 17/044,814

(22) PCT Filed: Apr. 5, 2019

(86) PCT No.: PCT/EP2019/058722
§ 371 (c)(1),
(2) Date: Oct. 1, 2020

(87) PCT Pub. No.: WO2019/193190
PCT Pub. Date: Oct. 10, 2019

(65) Prior Publication Data
US 2021/0094895 A1 Apr. 1, 2021

(30) Foreign Application Priority Data
Apr. 6, 2018 (EP) ..................... 18166169

(51) Int. Cl.
*C07C 7/00* (2006.01)
*B01D 3/14* (2006.01)
(Continued)

(52) U.S. Cl.
CPC .............. *C07C 7/005* (2013.01); *B01D 3/146* (2013.01); *B01D 5/0036* (2013.01);
(Continued)

(58) Field of Classification Search
CPC .. C07C 7/005; C07C 7/09; C07C 7/11; B01D 3/146; B01D 5/0036; B01D 5/0063;
(Continued)

(56) References Cited

U.S. PATENT DOCUMENTS

| 4,157,905 A | 6/1979 | Hengstebeck |
| 5,253,479 A | 10/1993 | Di Cintio et al. |

FOREIGN PATENT DOCUMENTS

| EP | 0683146 A1 | 11/1995 |
| EP | 1215459 A2 | 6/2002 |
| EP | 3136028 A1 | 3/2017 |

OTHER PUBLICATIONS

Translation of EP 3136028 A (Year: 2017).*
(Continued)

*Primary Examiner* — Ali Z Fadhel
(74) *Attorney, Agent, or Firm* — Cozen O'Connor

(57) ABSTRACT

The invention relates to a process for separating a component mixture (K) comprising hydrogen, methane, hydrocarbons having two carbon atoms and hydrocarbons having three or more carbon atoms, wherein in a deethanization at least a portion of the component mixture (K) is subjected to a first partial condensation by cooling from a first temperature level to a second temperature level at a first pressure level to obtain a first gas fraction (G1) and a first liquid fraction (C1), at least a portion of the first gas fraction (G1) is subjected to a second partial condensation by cooling from the second temperature level to a third temperature level at the first pressure level to obtain a second gas fraction (G4) and a second liquid fraction (C2), and at least a portion of the first liquid fraction (C1) and at least a portion of the second liquid fraction (C2) are subjected to a rectification to obtain a third gas fraction (G3) and a third liquid fraction (C3+). The first liquid fraction (C1) or its part subjected to the rectification and the second liquid fraction (C2) or its part subjected to the rectification are expanded to a second pressure level and the rectification is carried out at the second pressure level, the first pressure level being 25 to 35 bar and the second pressure level being 14 to 17 bar. An overhead gas formed during the rectification is cooled to −25
(Continued)

to −35° C. and partially condensed, wherein a condensed portion of the overhead gas is used partially or completely as a reflux in the rectification and an uncondensed portion of the overhead gas is provided partially or completely as the third gas fraction (G3). The present invention likewise provides a corresponding plant (100, 200).

15 Claims, 3 Drawing Sheets

(51) Int. Cl.
　　*B01D 5/00*　　(2006.01)
　　*B01D 53/00*　　(2006.01)
　　*C07C 7/09*　　(2006.01)
　　*C07C 7/11*　　(2006.01)
　　*C10G 70/04*　　(2006.01)

(52) U.S. Cl.
　　CPC ......... *B01D 5/0063* (2013.01); *B01D 5/0075* (2013.01); *B01D 5/009* (2013.01); *B01D 53/002* (2013.01); *C07C 7/09* (2013.01); *C07C 7/11* (2013.01); *C10G 70/043* (2013.01)

(58) Field of Classification Search
　　CPC .... B01D 5/0075; B01D 5/009; B01D 53/002; C10G 70/043; F25J 2200/50; F25J 2200/70; F25J 2200/74; F25J 2205/04; F25J 2210/12; F25J 2215/62; F25J 2240/02; F25J 2270/04; F25J 2270/12; F25J 2270/60; F25J 3/0233; F25J 3/0238; F25J 3/0242; F25J 3/0252; F25J 3/0219
　　See application file for complete search history.

(56) References Cited

OTHER PUBLICATIONS

PCT/EP2019/058722 International Search Report dated Jun. 17, 2019; 2 pages.
PCT/EP2019/058722 International Preliminary Report on Patentability dated Aug. 13, 2020; 9 pages.
Indonesian Patent Application No. P00202008287, Office Action with English translation, dated Aug. 2, 2022, 5 pages.
Chinese Patent Application No. 201980024786.1, English Translation of Office Action, dated Jan. 6, 2022, 10 pages.
Chinese Patent Application No. 201980024786.1, Office Action, dated Jan. 6, 2022, 8 pages.

* cited by examiner

PROCESS AND PLANT FOR SEPARATION OF A HYDROCARBON MIXTURE

The invention relates to a process and a plant for separation of a component mixture according to the preambles of the independent claims.

STATE OF THE ART

Processes and apparatuses for steamcracking of hydrocarbons are known and are described, for example, in the article "Ethylene" in Ullmann's Encyclopedia of Industrial Chemistry, online since 15 Apr. 2007, DOI 10.1002/14356007.a10_045.pub2.

By steamcracking, but also using other processes and apparatuses, hydrocarbon mixtures are obtained. These have to be separated at least partly into the components present in each case. This can be effected in separation sequences of different kinds. Corresponding separation sequences include, after prior removal of water, heavy components and sour gases, demethanizers, deethanizers and depropanizers (see especially section 5.3.2.2 "Hydrocarbon Fractionation Section" in the Ullmann article mentioned). The sequence of demethanization, deethanization and depropanization may vary in this connection.

A process and an apparatus for separation of a corresponding gas mixture in which a first fraction comprising predominantly or exclusively methane and hydrogen (C1minus fraction), a fraction containing predominantly or exclusively hydrocarbons having two carbon atoms (C2 fraction) and a fraction containing predominantly or exclusively hydrocarbons having three or more carbon atoms (C3 plus fraction) are formed are illustrated in FIG. 1 and elucidated below with reference to said figure. In this case, deethanization is followed by demethanization, using rectification columns for both process steps. The terms demethanization and deethanization are customary in the field, and the specialist is familiar with devices used for demethanization and deethanization.

Advantages of this process or this plant are a simple process regime and high energy efficiency. Disadvantages, by contrast, are the complexity of the deethanization with an additional C3 absorber and the complexity of the demethanization with intermediate cooler and top condenser disposed above the demethanization column. The latter entail elevated instrumentation complexity and safety expenditure. A process in which such a C3 absorber is used is also known from EP 0 683 146 A1.

According to FIG. 2, U.S. Pat. No. 5,253,479 A discloses a process in which a gaseous component mixture is subjected to a first cooling at 36 bar. The first cooling is to −30 to −40° C. After the first cooling, a first phase separation takes place in a first vessel. The gas phase from the first vessel is subjected to a second cooling, namely to −45° C. This second cooling is followed by a second phase separation in a second vessel. The liquid phases from the first and second vessel are fed into a column operated at 30 bar. In a process disclosed in EP 1 215 459 A2 at least comparable pressures are used.

The problem addressed by the present invention is therefore that of specifying improved measures for separation of corresponding gas mixtures.

DISCLOSURE OF THE INVENTION

Against this background, the invention proposes a process and a plant for separation of a component mixture having the respective features of the independent claims. Preferred embodiments are the subject of the dependent claims and of the description which follows.

Before the features and advantages of the present invention are elucidated, the basics thereof and the terms used will be elucidated.

The present invention is used for separation of component mixtures comprising predominantly or exclusively hydrogen, methane, hydrocarbons having two carbon atoms (ethane, ethylene and possibly acetylene if it has not already been converted in a preceding hydrogenation), and hydrocarbons having three or more carbon atoms (propane, propylene, possibly methylacetylene and heavier hydrocarbons having four, five, six or more carbon atoms in particular).

In the context of the present invention, corresponding component mixtures are especially formed using a steamcracking process. In the steamcracking process, what is called a crude gas or cracked gas is obtained, which also includes further components as well as the components mentioned. These, especially water, sour gases such as carbon dioxide and hydrogen sulfide, and gasoline- and oil-like components, can be separated upstream of the process proposed in accordance with the invention or a corresponding plant. Further process steps may also be performed upstream of the process proposed in accordance with the invention or a corresponding plant, especially a hydrogenation of acetylenes (called "front-end hydrogenation"). The component mixture processed in the context of the present invention is in the compressed state and is typically at ambient temperature.

In the specialist field, abbreviations that specify the carbon number of the hydrocarbons present predominantly or exclusively in each case are used for fractions that are formed from the component mixtures mentioned in corresponding processes. Thus a "C1 fraction" is a fraction containing predominantly or exclusively methane (but by convention in some cases also hydrogen, then also referred to as "C1minus fraction"). By contrast a "C2 fraction" contains predominantly or exclusively ethane, ethylene and/or acetylene. A "C3 fraction" contains predominantly propane, propylene, methylacetylene and/or propadiene. The same applies correspondingly to a "C4 fraction" and the higher fractions. Multiple fractions may also be combined in terms of process and/or designation. For example a "C2plus fraction" contains predominantly or exclusively hydrocarbons having two or more carbon atoms and a "C2minus fraction" contains predominantly or exclusively hydrocarbons having one or two carbon atoms and optionally hydrogen.

In the terminology used here, component mixtures may be rich or poor in one or more components, wherein "rich" may represent a content of at least 90%, 95%, 99%, 99.5%, 99.9%, 99.99% or 99.999% and "poor" may represent a content of not more than 10%, 5%, 1%, 0.1%, 0.01% or 0.001% on a molar, weight or volume basis. In the terminology used here, component mixtures may also be enriched or depleted of one or more components, where these terms relate to a corresponding content in another component mixture (starting mixture) from which the component mixture has been obtained. The component mixture is "enriched" when it contains not less than 1.1 times, 1.5 times, 2 times, 5 times, 10 times, 100 times or 1000 times the content, and "depleted" when it contains not more than 0.9 times, 0.5 times, 0.1 times, 0.01 times or 0.001 times the content, of a corresponding component, based on the starting mixture. If it is said here that a component mixture contains "essentially" or "at least predominantly" one or more components, this is especially understood to mean that the component mixture is at least rich in the one or more components in the above-elucidated sense or includes exclusively the one or more components.

A component mixture is "derived" or "formed" from a starting mixture when it includes at least some components present in or obtained from the starting mixture. A component mixture derived or formed in this way may be obtained or formed from the starting mixture by separating off or branching off a substream or one or more components, enriching or depleting with regard to one or more components, chemically or physically converting one or more components, heating, cooling, pressurizing and the like.

For characterization of pressures and temperatures, the present application uses the terms "pressure level" and "temperature level", by means of which it is intended to express the fact that corresponding pressures and temperatures in a corresponding plant need not be used in the form of exact pressure and temperature values in order to implement the concept of the invention. However, such pressures and temperatures typically vary within particular ranges of, for example, ±1%, 5%, or 10% around a mean value. It is possible here for corresponding pressure levels and temperature levels to lie in disjoint ranges or in overlapping ranges. In particular, pressure levels encompass, for example, pressure drops that are unavoidable or to be expected, for example on account of cooling effects. The same holds for temperature levels. The pressure levels indicated here in bar are absolute pressures.

A "heat exchanger" serves for indirect transfer of heat between at least two streams being guided, for example, in countercurrent to one another, for example a warmer gaseous compressed stream and one or more colder liquid streams. A heat exchanger may be formed from a single heat exchanger section or a plurality of parallel- and/or series-connected heat exchanger sections, for example from one or more plate heat exchanger blocks. A heat exchanger has "passages" formed as separate fluid channels with heat exchange surfaces.

In the terminology used here, a "rectification column" is a separation unit set up for at least partial fractionation of a mixture of matter (fluid) provided in gaseous or liquid form or in the form of a biphasic mixture having liquid and gaseous components, possibly even in the supercritical state, i.e. for producing pure substances or substance mixtures in each case from the mixture of matter that are enriched/depleted or rich/poor with regard to at least one component compared to the mixture of matter in the sense elucidated above. Rectification columns are sufficiently well known from the field of separation technology. Rectification columns typically take the form of cylindrical metal vessels equipped with internals, for example sieve trays or ordered and unordered packings. One feature of a rectification column is that a liquid fraction separates out in its lower region, also referred to as the bottom. This liquid fraction, which is referred to here as bottoms liquid, is heated in a rectification column by means of a reboiler, such that a portion of the bottoms liquid is evaporated continuously and ascends in gaseous form in the rectification column. A rectification column is also provided with what is called a tops condenser into which at least a portion of a gas mixture which accumulates in an upper region of the rectification column or a corresponding pure gas, referred to here as tops gas is fed, is liquefied in part to give a condensate and is applied as liquid return stream at the top of the rectification column. A portion of the condensate obtained from the tops gas can be used in some other way.

A "stripping column" differs from a rectification column essentially by the absence of a tops condenser and the lack of use of a return stream formed from tops gas for separation. However, it is possible for liquids that give a certain return flow or by means of which a liquid fraction descending in the stripping column in exchange with a gas phase is provided to be fed into a stripping column at different heights. However, a stripping column as used in the context of the present invention is an apparatus operated without internal tops gas condensate.

With regard to the design and specific configuration of rectification columns and other separation columns, reference is made to relevant textbooks (see, for example, Sattler, K: Thermische Trennverfahren: Grundlagen, Auslegung, Apparate [Thermal Separation Processes: Basics, Design, Apparatuses], 3rd edition 2001, Weinheim; Wiley-VCH).

Advantages of the Invention

Overall, the present invention proposes a process for separating a component mixture comprising hydrogen, methane, hydrocarbons having two carbon atoms and hydrocarbons having three or more carbon atoms. The process comprises a deethanization and a demethanization, wherein the demethanization is subsequent to the deethanization. In the process, as known in this respect, firstly, in the deethanization, at least 95%, 96%, 97%, 98% or 99% of the hydrocarbons having three or more carbon atoms are separated from at least a portion of the component or gas mixture and then, in the demethanization, at least 95%, 96%, 97%, 98% or 99% of the methane and the hydrogen are separated from the remaining residue. In order to avoid misunderstandings, it should be stressed that the "remaining residue" from deethanisation is understood here as the fraction consisting predominantly or exclusively of hydrocarbons with two carbon atoms, methane and hydrogen. The present invention thus relates to what is called a deethanizer-first or front-end-deethanizer process, as known in principle from the prior art.

In the context of the invention, at least a portion of the component mixture is subjected here to a first partial condensation by cooling from a first temperature level to a second temperature level at a first pressure level to obtain a first gas fraction and a first liquid fraction. The first gas fraction and the first liquid fraction are formed by purely condensative means here in the course of the partial condensation. "Purely condensative" formation is more particularly understood to mean that no return stream, i.e. no absorption liquid for scrubbing out particular components, is used in the formation of the first gas fraction and the first liquid fraction. A total amount of the first gas fraction formed within a particular period of time and the first liquid fraction formed within the same period of time thus corresponds, in the context of the present invention, to the amount of the component mixture which is used to form the first gas fraction and the first liquid fraction. In this aspect, the process according to the invention thus differs from processes for deethanization according to the prior art in which "C3 absorbers" are used. In a C3 absorber, a first gas fraction and a first liquid fraction are likewise formed, but with feeding of a return stream in order to scrub out hydrocarbons having three carbon atoms that have not condensed completely out of the gas phase.

The component mixture that has been subjected to the cooling from the first temperature level to the second temperature level at the first pressure level especially includes 32 to 36 mole percent of hydrogen, 5 to 8 mole percent of methane, up to 57 mole percent of hydrocarbons having two carbon atoms and up to 4 mole percent of hydrocarbons having three or more carbon atoms. The present invention is thus particularly suitable for those gas mixtures that come from processes for steamcracking of gaseous feeds. A gaseous feed comprises predominantly or exclusively ethane, or ethane and propane. The first gas fraction formed in the first partial condensation especially includes 43 to 47 mole percent of hydrogen, 7 to 9 mole percent of methane, 42 to 45 mole percent of hydrocarbons having two carbon atoms and 0.5 to 0.7 mole percent of hydrocarbons having three or more carbon atoms. The first liquid fraction formed in the first partial condensation especially includes 1 to 2 mole percent of hydrogen, 2 to 3 mole percent of methane, 82 to 85 mole percent of hydrocarbons having two carbon atoms and 10 to 13 mole percent of hydrocarbons having three or more carbon atoms. In other words, the first gas fraction still contains significant amounts of hydrocarbons having three or more carbon atoms that are to be recovered. In the context of the present invention, this is effected as elucidated hereinafter.

In the context of the present invention, at least a portion of the first gas fraction is subjected to a second partial condensation by cooling from the second temperature level to a third temperature level at the first pressure level to obtain a second gas fraction and a second liquid fraction. In the context of the second partial condensation, the hydrocarbons having three or more carbon atoms that were present in the first gas fraction beforehand are separated out down to possible residual contents. The second gas fraction formed in the second partial condensation especially includes 59 to 62 mole percent of hydrogen, 9 to 11 mole percent of methane, 29 to 31 mole percent of hydrocarbons having two carbon atoms and 0.6 to 0.9 mole percent of hydrocarbons having three or more carbon atoms. The second liquid fraction formed in the second partial condensation especially includes 1.5 to 2 mole percent of hydrogen, 3 to 4 mole percent of methane, 89 to 92 mole percent of hydrocarbons having two carbon atoms and 2 to 3 mole percent of hydrocarbons having three or more carbon atoms. The formation of the second gas fraction and the second liquid fraction is also carried out purely condensatively, i.e. without the use of absorbers as explained above.

The measures in the context of the invention further comprise that at least a portion of the first liquid fraction and at least a portion of the second liquid fraction are subjected to a rectification to obtain a third gas fraction and a third liquid fraction. For this rectification, it is possible to use a rectification column which is referred to hereinafter and especially also in the description of the figures as deethanization column. The terms are used here synonymously. In the bottom of a corresponding rectification column, the hydrocarbons having three or more carbon atoms are essentially separated out, such that the tops gas from the rectification column which is used to form the third gas fraction is essentially free of such components.

In the context of the present invention, the second gas fraction (after the second partial condensation from the second to the third temperature level), but also the third gas fraction (from the rectification) are formed in such a way that they include more than 95%, 96%, 97%, 98% or 99% hydrogen, methane and hydrocarbons having two carbon atoms. On the other hand, the third liquid fraction is formed in the context of the present invention such that it includes more than 95%, 96%, 97%, 98% or 99% hydrocarbons having three or more carbon atoms.

In the context of conventional deethanization steps, two gas fractions are formed as well, but are drawn off here, as also illustrated in connection with FIG. 1, from the top of a C3 absorber and from the top of a deethanization column. The C3 absorber is not required in the context of the present invention, and so a process according to the invention can be conducted with much lower complexity. In the context of the present invention, the C3 absorber is replaced by the first partial condensation in combination with the second partial condensation of the gas fraction formed from the second to the third temperature level at the first pressure level, in which the second liquid fraction formed by the second partial condensation (rather than a stream of matter formed from a C3 absorber, as illustrated in FIG. 1) is guided into the rectification column, where it is separated to form the third gas fraction and the third liquid fraction. The process according to the invention can be implemented without any significant alterations in the process steps downstream of the deethanization, since the heat exchangers, coolants etc. that are used for the first and second partial condensation are already present in a corresponding process or a corresponding plant and can therefore continue to be used.

According to the invention, the first liquid fraction or its part subjected to the rectification and the second liquid fraction or its part subjected to the rectification are expanded from the first pressure level to a second pressure level before the rectification and the rectification is carried out at the second pressure level, the first pressure level being 25 to 35 bar and the second pressure level 14 to 17 bar. The present invention therefore uses relatively low pressures compared to the condensation steps in rectification.

Due to the lower pressures used in rectification for deethanization within the scope of the present invention, the condensation power required for condensing the overhead gas is much lower than at higher pressures. Therefore, one can work with a top-attached head condenser within the scope of the present invention. No reflux vessel outside the column used for rectification and no pump are required to provide a reflux for rectification. In addition, at lower pressures, fouling in the sump and in the boiler of the column used is greatly reduced.

The present invention also makes it possible to provide a rectification reflux using C3 refrigeration only. Therefore, according to the invention, an overhead gas formed during rectification is cooled to (only) −25 to −35° C. and is partially condensed, wherein a condensed portion of the overhead gas is used partially or completely as a rectification reflux and a non-condensed portion of the overhead gas is provided partially or completely as the third gas fraction.

The condensed portion of the overhead gas is advantageously returned to the rectification column used for rectification without the use of a reflux pump and/or an external reflux vessel, and the head condenser is advantageously placed on top of the column. This means, in particular, that the reflux is fed to the column in the form of the condensed fraction or a correspondingly used portion thereof without the use of tubings extending to the outside of the column.

In the process according to the invention, the first pressure level is especially 25 to 35 bar abs., more especially 28 to 30 bar abs., for example about 29 bar abs. In the context of the present invention, the second pressure level may especially be 12 to 16 bar abs., for example about 14 bar abs.

In the process according to the invention, the first temperature level is especially 0 to 50° C., more especially 10 to 30° C., for example about 20° C., i.e. essentially ambient temperature. In the context of the present invention, the second temperature level may especially be −30 to −40° C., more especially −33 to −37° C., for example about −35° C. Corresponding cooling to the second temperature level can especially be effected using a suitable C3 (propylene) coolant in a corresponding heat exchanger. In the context of the present invention, cooling to the second temperature level can be accomplished by additionally using streams of matter or component mixtures in the process or in downstream processes, for example a component mixture of predominantly or exclusively hydrogen and methane formed in the process (which is described hereinafter as a fraction containing more than 95% hydrogen and methane from a further separation apparatus) and a fraction formed in a downstream separation step (C2 splitter) comprising predominantly or exclusively ethane.

In the context of the present invention, the third temperature level may especially be −50 to −60° C., more especially −52 to −56° C., for example about −54° C. Corresponding cooling to the third temperature level can especially be effected using a suitable "high-pressure" C2 (ethylene) coolant in a corresponding heat exchanger. A corresponding coolant is especially at a pressure level of 8 to 9 bar abs. In the context of the present invention, cooling to the third temperature level can likewise be accomplished by additionally using streams of matter or component mixtures in the process or in downstream processes, for example the component mixture, formed in the process, of predominantly or exclusively hydrogen and methane and the fraction formed in the downstream separation step (C2 splitter) comprising predominantly or exclusively ethane. In addition, for the cooling to the third temperature level, it is also possible to use a component mixture which is formed in the process and then guided into a downstream separation step (demethanization), including predominantly or exclusively hydrocarbons having two carbon atoms. The cooling to the third temperature level is especially also effected in countercurrent to the already mentioned liquid fraction formed in the second partial condensation.

In the context of the present invention, the third gas fraction is formed in the rectification due to the measures according to the invention especially at a temperature level of −25 to −35° C., more especially from −28 to −32° C., for example about −30° C. These are the temperatures used for condensation of the overhead gas of the corresponding column. This can, as mentioned, especially be effected in connection with a condensation of tops gas with a suitable C3 (propylene) coolant. In other words, in the context of the present invention, a rectification column which is cooled with a tops condenser which is operated with propylene coolant is especially used for the rectification. In the context of the present invention, the third liquid fraction is formed in the rectification advantageously at a temperature level of 65 to 75° C., more especially 68 to 72° C., for example about 70° C. This can especially be achieved by the use of a reboiler operated with low-pressure steam, for example.

In the context of the present invention, the second gas fraction and the third gas fraction that have already been essentially freed of hydrocarbons having three or more carbon atoms in the process steps described above are fed to a downstream demethanization. This especially forms a fraction containing more than 95%, 96%, 97%, 98% or 99% hydrogen and methane and a fraction containing more than 95%, 96%, 97%, 98% or 99% hydrocarbons having two carbon atoms from at least a portion of the second gas fraction and of the third gas fraction in a further separation apparatus, namely a stripping column. In the context of the present invention, such a separation is effected in a particularly advantageous manner because, in particular, a separation apparatus in which no above-described complex condensation of gas from the separation apparatus is necessary is used here. The separation apparatus in the form of a stripping column is thus operated without a tops condenser. The further separation apparatus is operated at the second pressure level, and a specific pressure used may also be slightly, i.e. up to 1, 2, 3, 4 or 5 bar, below the pressure which is used in the rectification to which the first and second liquid fractions are fed.

The feeding of the second gas fraction into the further separation apparatus may especially also be preceded upstream by a stepwise cooling operation. In a particularly preferred embodiment of the present invention, at least a portion of the second gas fraction is subjected here to further partial condensations by means of stepwise cooling via one or more intermediate temperature levels to a fourth temperature level at the first pressure level to obtain further liquid fractions. The liquid fractions formed in each case are advantageously fed into the separation apparatus, i.e. the stripping column, at different heights, in accordance with their respective contents of hydrogen, methane and hydrocarbons having two carbon atoms.

Advantageously, a proportion of the second gas fraction that remains in gaseous form at the fourth temperature level is expanded from the first pressure level to the second pressure level to provide refrigeration energy and fed into the further separation apparatus. The feeding is advantageously effected above each of the further liquid fractions that are obtained in the further partial condensations mentioned above the multiple intermediate temperatures.

In the context of the present invention, the fourth temperature level is especially −140 to −150° C., more especially −140 to −144° C., for example about −142° C. This temperature level can especially be achieved by means of a stream of matter which is formed from tops gas from the separation apparatus. Advantageously, the fraction containing more than 95%, 96%, 97%, 98% or 99% hydrogen and methane is thus taken from the further separation apparatus, expanded from the second pressure level to a third pressure level to provide refrigeration energy, and used for stepwise cooling to the fourth temperature level. The intermediate temperature levels may firstly especially be −70 to −80° C., more especially −76 to −78° C., for example about −77° C., and secondly −95 to −105° C., more especially −96 to −100° C., for example about −98° C. These temperature levels can be achieved, for example, firstly using "medium-pressure" C2 (ethylene) coolant at a pressure level of 3 to 4 bar, and secondly using "low-pressure" C2 (ethylene) coolant at a pressure level of 1.1 to 1.6 bar. In correspondingly used heat exchangers, it is also especially possible to use the fraction containing more than 95%, 96%, 97%, 98% or 99% hydrogen and methane from the further separation apparatus which has been expanded to the third pressure level and used beforehand for cooling to the fourth pressure level.

The concept described here can be used to simplify the complicated demethanization and deethanization in the recovery of the hydrocarbons having two carbon atoms especially from the cracking gas from an ethylene plant having gaseous feeds such as ethane and ethane/propane, and particularly the deethanization can be effected without the C3 absorber with attached tops condenser. The rectification used for deethanization is conducted at a low pressure, the second pressure level mentioned, such that the separation expenditure is reduced by more than 60%. Consequently, the deethanizer or a corresponding rectification column can be designed much smaller. The bottoms can be boiled up with washing water or low-pressure steam. This leads to simple operation, lower instrumentation complexity, less fouling, and lower capital and operating costs. The use of the present invention also makes it possible to use a simple stripping column rather than a complicated demethanization column. This likewise leads to simpler operation and lower instrumentation complexity and safety expenditure. The result is lower capital costs with constant energy consumption.

In a particularly preferred configuration of the process according to the invention, the separation apparatus, i.e. the stripping column, is operated with an internal heat exchanger which is cooled with a coolant a temperature level of −90 to −110° C. It is especially possible here to use the already mentioned "low-pressure" C2 (ethylene) coolant. This results in further advantages, which are more particularly that the third gas fraction from the rectification, for deethanization, has to be cooled to a lower temperature level, namely only to the third temperature level, whereas more intense cooling has to be effected in the absence of a corresponding internal heat exchanger. Moreover, it is possible to dispense with subcooling of a condensate formed from the second gas fraction.

The present invention also extends to a plant for separation of a component mixture comprising hydrogen, methane, hydrocarbons having two carbon atoms and hydrocarbons having three or more carbon atoms, wherein the plant has means for deethanization and means for demethanization, wherein the means for demethanisation are arranged downstream of the means for deethanization. As insofar known from the deethanization and the demethanization, the means for deethanization are set up to first separate at least 95%, 96%, 97%, 98% or 99% of the hydrocarbons having three or more carbon atoms from at least a portion of the gas mixture and the means for demethanization are set up to then separate at least 95%, 96%, 97%, 98% or 99% of the methane and the hydrogen from the remaining residue. The plant comprises means set up to subject at least a portion of the component mixture to a first partial condensation by cooling from a first temperature level to a second temperature level at a first pressure level to obtain a first gas fraction and a first liquid fraction, subject at least a portion of the first gas fraction to a second partial condensation by cooling from the second temperature level to a third temperature level at the first pressure level to obtain a second gas fraction and a second liquid fraction, and to subject at least a portion of the first liquid fraction and at least a portion of the second liquid fraction to a rectification to obtain a third gas fraction and a third liquid fraction According to the present invention, for the second partial condensation means are provided which are adapted to perform the second partial condensation such that the second gas fraction comprises more than 95%, 96%, 97%, 98% or 99% hydrogen, methane and hydrocarbons having two carbon atoms. In particular, the rectification is set up to form the third gas fraction with a corresponding content of hydrogen, methane and hydrocarbons with two carbon atoms, and to form the third liquid fraction (C3+) such that it comprises more than 95%, 96%, 97%, 98% or 99% hydrocarbons having three or more carbon atoms.

According to the invention, means are provided which are designed to expand the first liquid fraction or its part subject to rectification and the second liquid fraction or its part subject to rectification from the first pressure level to a second pressure level before the rectification. Such means may include, in particular, expansion valves. In addition, in accordance with the invention, means are provided which are designed to carry out the rectification at the second pressure level, the first pressure level being 25 to 35 bar and the second pressure level 14 to 17 bar. The latter means include, in particular, a column set up for rectification and designed to operate at that pressure.

Means are also be provided, in particular in the form of a head condenser mounted on top of the column used for rectification, which are arranged to cool an overhead gas formed during rectification to −25 to −35° C. and to partially condense it, and to use a condensed fraction of the overhead gas partially or completely as a reflux in the rectification and to provide a non-condensed fraction of the overhead gas partially or completely as the third gas fraction. In particular, these means are designed without external reflux vessels and pumps, as explained above.

A corresponding plant advantageously set up to perform a process as elucidated above in different configurations profits from the advantages mentioned, to which reference is explicitly made.

The invention is further elucidated hereinafter with reference to the appended drawings that illustrate configurations of the invention.

Figure 1:
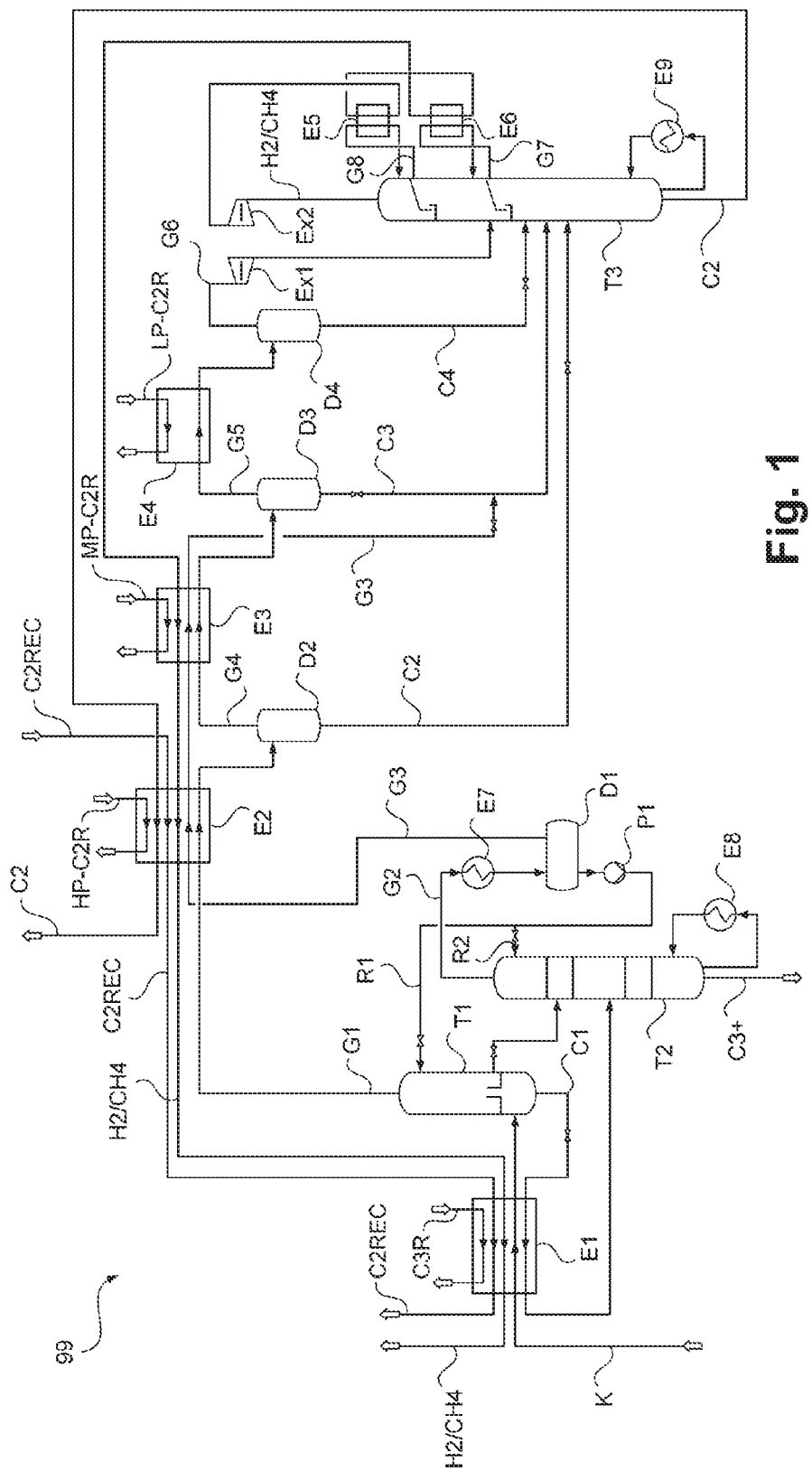
FIG. 1 illustrates a plant for separation of a component mixture.

In the figures, components that correspond to one another are given identical reference numerals. For the sake of clarity, there is no repeated elucidation of corresponding components. All pressure and temperature figures are approximate example values that may be within the ranges elucidated in detail above.

DETAILED DESCRIPTION OF THE DRAWINGS

FIG. 1 illustrates a noninventive plant for separation of a component mixture in the form of a simplified process flow diagram, collectively labelled 99.

The component mixture K, for example a cracking gas from a steamcracking process after drying, oil and gasoline removal, acid gas removal, compression and cracking gas hydrogenation, at 20° C. and 30 bar is first cooled down to −35° C. in a heat exchanger E1 against a hydrogen and methane fraction H2/CH4, an ethane fraction C2REC recycled from a C2 splitter (not shown), a condensate C1 from a C3 absorber T1 and a C3 coolant C3R, and then fed into a lower portion of the C3 absorber T1.

The C3 absorber T1 has a two-part design and has, as well as the lower portion, an upper portion. The two parts are separated from one another by means of a liquid barrier tray. A return stream R1 is applied to the upper portion; the condensate C1 mentioned is drawn off from the lower portion. After it has been heated in the heat exchanger E1, the condensate C1 is fed into a deethanization column T2. Likewise fed into the deethanization column T2 is a liquid that accumulates on the liquid barrier tray of the C3 absorber T1. A gas stream G1 is drawn off from the upper portion of the C3 absorber T1.

A gas stream G2 is drawn off from the top of the deethanizer column T2, cooled in a heat exchanger E7, for example by means of C3 coolant, and phase-separated in a vessel D1. A liquid phase that separates out in vessel D1 is conveyed by means of a pump P1 and recycled in the form of the return stream R1 mentioned to the C3 absorber T1 and in the form of a further return stream R2 to the deethanization column T2. A fraction uncondensed in vessel D1 is drawn off in the form of a gas stream G3.

Bottoms liquid from the deethanization column T2 is partly evaporated in a heat exchanger E8 which is operated, for example, by means of low-pressure steam, and recycled into the deethanization column T2. Further bottoms liquid is drawn off as liquid stream C3+ containing predominantly or exclusively hydrocarbons having three carbon atoms.

The gas streams G1 and G3 that have been essentially freed of hydrocarbons having three carbon atoms in this way are cooled in a second heat exchanger E2 against the hydrogen and methane fraction H2/CH4, the ethane fraction C2REC recycled from the C2 splitter (not shown), a fraction C2 guided into the C2 splitter and high-pressure C2 coolant HP-C2R. The gas stream G1 is partly condensed in this way and fed into a vessel D2 for phase separation. A liquid phase that separates out in vessel D2 is fed in the form of a liquid stream C2 into a demethanization column T3. A fraction uncondensed in vessel D2 is drawn off as gas stream G4.

The gas stream G4 and any already partly condensed gas stream G3 are cooled in a third heat exchanger E3 against the hydrogen and methane fraction H2/CH4 and medium-pressure C2 coolant MP-C2R. The gas stream G4 is partly condensed in this way and fed into a vessel D3 for phase separation. A liquid phase that separates out in vessel D3, after combination with the condensed gas stream G3, is fed as liquid stream C3 into the demethanization column T3. A fraction of gas stream G4 uncondensed in vessel D3 is drawn off in the form of a gas stream G5.

The gas stream G5 is cooled in a fourth heat exchanger E4 against low-pressure C2 coolant LP-C2R. The gas stream G5 is partly condensed in this way and fed into a vessel D4 for phase separation. A liquid phase that separates out in vessel D4 is fed as liquid stream C4 into the demethanization column T3. A fraction of gas stream G5 uncondensed in vessel D4 is drawn off as gas stream G6. The gas stream G6 is expanded in an expander Ex1 and fed into the demethanization column T3.

The demethanization column T3 has a multipart design and comprises a lower section, a middle section and an upper section. The hydrogen and methane fraction H2/CH4 is drawn off from the top of the demethanization column T3 or the upper section thereof, expanded in an expander Ex2 and guided through heat exchangers E5 and E6 for cooling. In heat exchangers E5 and E6, gas streams G7, G8 are respectively drawn off from an upper region of the lower and middle sections of the demethanization column T3, at least partly condensed and recycled as return stream to the corresponding sections of the demethanization column T3. Bottoms liquid from the demethanization column T3 is partly evaporated in a heat exchanger E9 which is operated, for example, by means of high-pressure C2 coolant, and recycled into the demethanization column T3. Further bottoms liquid is drawn off as liquid stream C2.

As mentioned, the complexity of the deethanization with the C3 absorber T1 and the complexity of the demethanization with the intermediate cooler in the form of heat exchanger E6 and the heat exchangers E5 and E6 arranged above the demethanization column is disadvantageous here. The latter entail elevated instrumentation complexity and safety expenditure.

Figure 2:
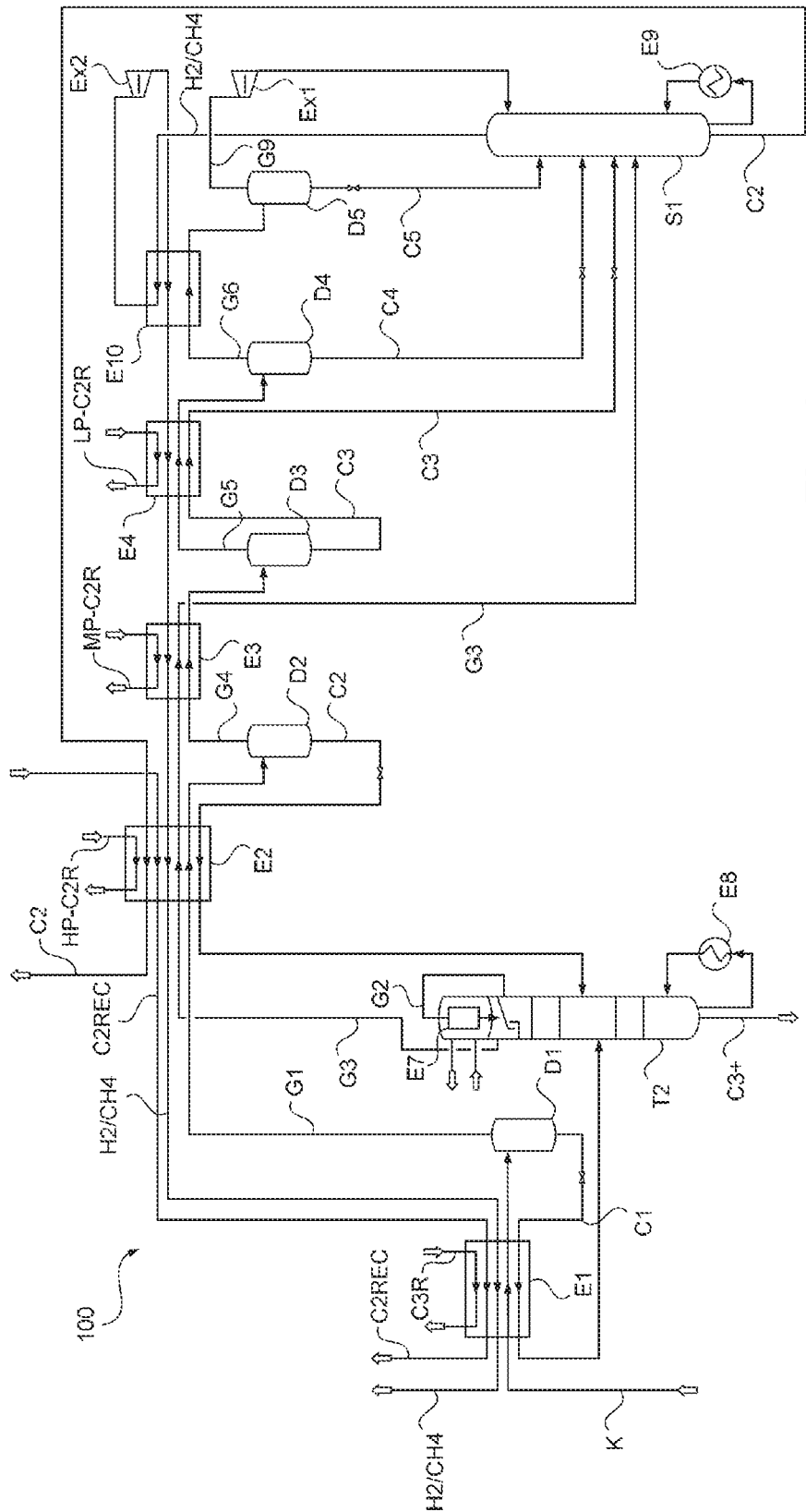
FIG. 2 illustrates a plant for separation of a component mixture in one embodiment of the invention.

FIG. 2 illustrates a plant for separation of a component mixture in one embodiment of the invention in the form of a simplified process flow diagram, collectively labelled 100.

The cooling in the first heat exchanger E1 is effected as elucidated for plant 99 in FIG. 1. Downstream of the heat exchanger E1, however, there is no C3 absorber T1 provided here, but merely a vessel D1 into which the component mixture K partly condensed in the first heat exchanger E1 is fed. A gas stream also labelled G1 here from the vessel D1 may therefore still include residual contents of hydrocarbons having three carbon atoms. However, after further cooling in the second heat exchanger E2, which is undertaken in a basically identical manner to that in the second heat exchanger E2 of the plant 99 according to FIG. 1, these separate out and can be recovered in the liquid stream also labelled C2 here. Liquid stream C2 further includes primarily hydrocarbons having two or three carbon atoms and also smaller amounts of hydrogen and methane.

Liquid stream C2 is therefore recycled through the second heat exchanger E2 and fed through a deethanization column also labelled T2 here. Tops gas from the deethanization column T2 in the plant 100 according to FIG. 2, by contrast with the deethanization column T2 of plant 99 according to FIG. 1, is likewise drawn off in the form of gas stream G2, cooled by means of C3 coolant and partly condensed, but the condensate formed is recycled only to the deethanization column T2 itself and not to a C3 absorber. An uncondensed fraction of gas stream G2 is drawn off in the form of stream of matter G3, which is now essentially free of hydrocarbons having three carbon atoms. Stream of matter G3 is first treated essentially like stream of matter G3 in plant 99 according to FIG. 1.

Here too, gas stream G4 and any already partly condensed gas stream G3 are cooled in a third heat exchanger E3 against the hydrogen and methane fraction H2/CH4 and medium-pressure C2 coolant MP-C2R. Here too, the gas stream G4 is partly condensed and fed into a vessel D3 for phase separation. A liquid phase which separates out in vessel D3 is drawn off in the form of a liquid stream C3 and a fraction of gas stream G4 uncondensed in vessel D3 in the form of a gas stream G5.

Gas stream G5 and liquid stream C3 are (sub)cooled here in a fourth heat exchanger E4 against the hydrogen and methane fraction H2/CH4 and low-pressure C2 coolant LP-C2R. The gas stream G5 is partly condensed in this way and fed into a vessel D4 for phase separation. A liquid phase that separates out in vessel D4 is subsequently fed as liquid stream C4 into a stripping column S1, as is liquid stream C3. A fraction of gas stream G5 uncondensed in vessel D4 is drawn off as gas stream G6.

However, gas stream G6 is now, by contrast with plant 99 according to FIG. 1, cooled down in a further heat exchanger E10 which is cooled with expanded tops gas from stripping column S1, i.e. the hydrogen and methane fraction H2/CH4. Gas stream G6 that has been partly condensed in this way is phase-separated in a further vessel D5. It is only a gas phase that remains here that is expanded by an expander, also labelled Ex1 here, and fed into the stripping column S1. The liquid phase that separates out in the further vessel D5 is likewise fed in the form of a liquid stream C5 into the stripping column S1.

The stripping column S1 has a one-part design and has only a reboiler. The hydrogen and methane fraction H2/CH4 is drawn off from the top of the stripping column S1, in an expander labelled Ex2 here too. The heat exchangers E5 and E6 of plant 99 according to FIG. 1 are now replaced by the heat exchanger 10. The hydrogen and methane fraction H2/CH4 is guided through heat exchangers E10, E4, E3, E2 and E1. Bottoms liquid from the stripping column S1 is partly evaporated in a heat exchanger E9 which is operated, for example, by means of high-pressure C2 coolant, and recycled into the stripping column S1. Further bottoms liquid is drawn off as liquid stream C2.

Figure 3:
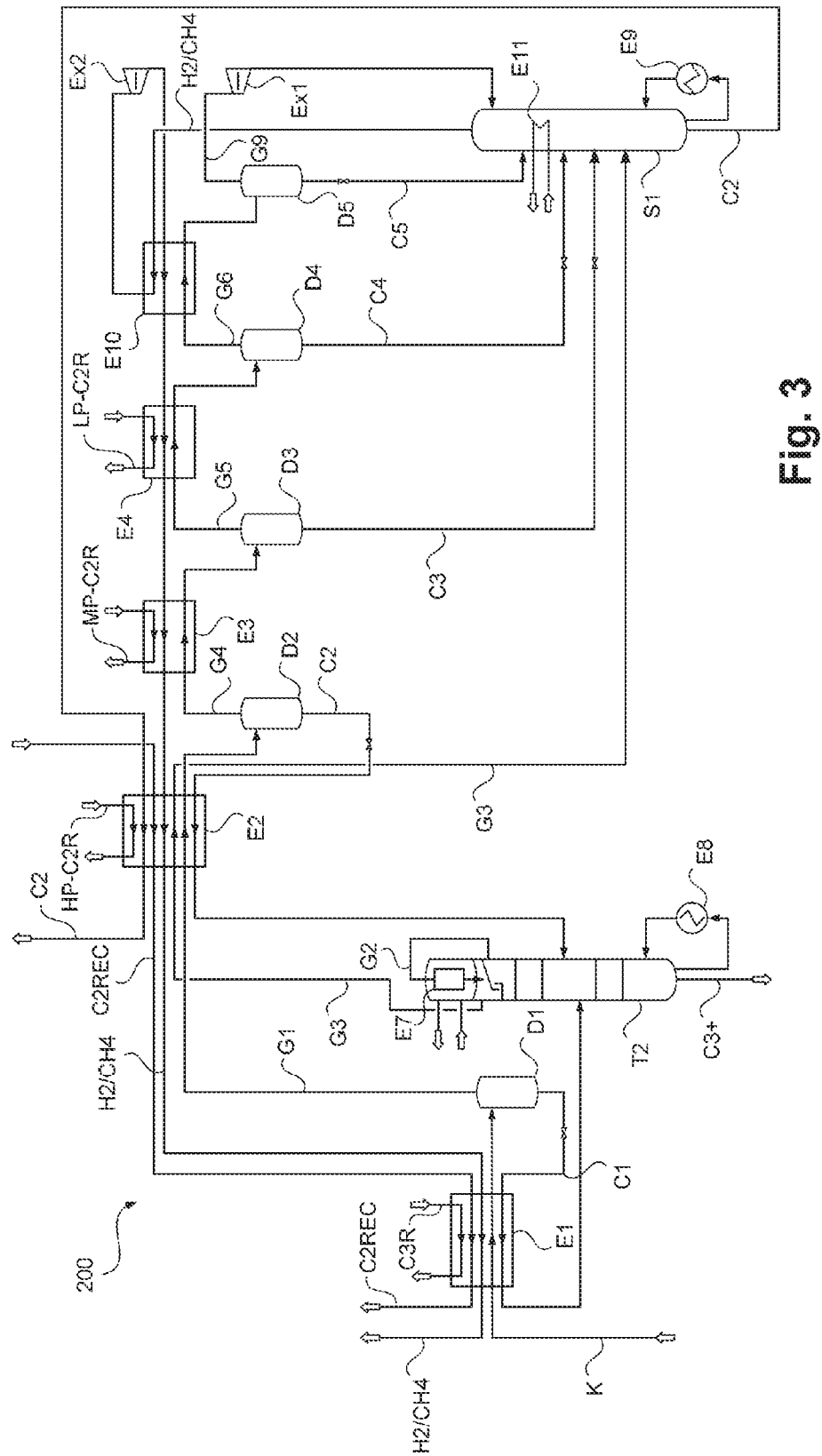
FIG. 3 illustrates a plant for separation of a component mixture in one embodiment of the invention.

FIG. 3 illustrates a plant for separation of a component mixture in one embodiment of the invention in the form of a simplified process flow diagram, collectively labelled 200.

The plant 200 illustrated in FIG. 3 differs from the plant 100 illustrated in FIG. 2 particularly in that there is a further heat exchanger E11 integrated into the stripping column S1, which is cooled with low-pressure C2 coolant. The heat exchanger E11 is provided between the feed points of condensates C4 and C5 from vessels D4 and D10. By this measure, the tops gas from the deethanization column T2, i.e. the gas stream G3 after cooling in the second heat exchanger E2, can be introduced directly into the stripping column S1, and the condensate from vessel D3, i.e. the liquid stream C3, need not be subcooled in the fourth heat exchanger E4. As a result, the consumption of medium-pressure and low-pressure C2 coolant in the third heat exchanger E3 and in the fourth heat exchanger E4 is greatly reduced, and hence the total consumption of C2 coolant.

The invention claimed is:

1. Process for separating a component mixture (K) comprising hydrogen, methane, hydrocarbons having two carbon atoms and hydrocarbons having three or more carbon atoms, comprising a deethanization and a demethanization subsequent to the deethanization, wherein
   in the deethanization at least a portion of the component mixture (K) is subjected to a first partial condensation by cooling from a first temperature level to a second temperature level at a first pressure level to obtain a first gas fraction (G1) and a first liquid fraction (C1),
   in the deethanization at least a portion of the first gas fraction (G1) is subjected to a second partial condensation by cooling from the second temperature level to a third temperature level at the first pressure level to obtain a second gas fraction (G4) and a second liquid fraction (C2),
   in the deethanization at least a portion of the first liquid fraction (C1) and at least a portion of the second liquid fraction (C2) is subjected to a rectification to obtain a third gas fraction (G3) and a third liquid fraction (C3+),
   the second partial condensation is performed such that the second gas fraction (G4) contains more than 95% hydrogen, methane and hydrocarbons having two carbon atoms,
   the first liquid fraction (C1) or its part subjected to the rectification and the second liquid fraction (C2) or its part subjected to the rectification are expanded from the first pressure level to a second pressure level before the rectification and the rectification is carried out at the second pressure level, the first pressure level being 25 to 35 bar and the second pressure level being 14 to 17 bar, and
   an overhead gas formed in the rectification is cooled to −25 to −35° C. and thereby partially condensed, wherein a condensed portion of the overhead gas is used partially or completely as a reflux in the rectification and an uncondensed portion of the overhead gas is provided partially or completely as the third gas fraction (G3),
   characterized in that
   the rectification is carried out using a rectification column (T2), the condensed proportion of the overhead gas or its portion being fed back to the rectification column (T2) without using a reflux pump and/or a reflux vessel arranged outside the column.

2. Process for separating a component mixture (K) comprising hydrogen, methane, hydrocarbons having two carbon atoms and hydrocarbons having three or more carbon atoms, comprising a deethanization and a demethanization subsequent to the deethanization, wherein
   in the deethanization at least a portion of the component mixture (K) is subjected to a first partial condensation by cooling from a first temperature level to a second temperature level at a first pressure level to obtain a first gas fraction (G1) and a first liquid fraction (C1),
   in the deethanization at least a portion of the first gas fraction (G1) is subjected to a second partial condensation by cooling from the second temperature level to a third temperature level at the first pressure level to obtain a second gas fraction (G4) and a second liquid fraction (C2),
   in the deethanization at least a portion of the first liquid fraction (C1) and at least a portion of the second liquid fraction (C1) is subjected to a rectification to obtain a third gas fraction (G3) and a third liquid fraction (C3+),
   the second partial condensation is performed such that the second gas fraction (G4) contains more than 95% hydrogen, methane and hydrocarbons having two carbon atoms,
   the first liquid fraction (C1) or its part subjected to the rectification and the second liquid fraction (C2) or its part subjected to the rectification are expanded from the first pressure level to a second pressure level before the rectification and the rectification is carried out at the second pressure level, the first pressure level being 25 to 35 bar and the second pressure level being 14 to 17 bar, and
   an overhead gas formed in the rectification is cooled to only−25 to −35° C. and thereby partially condensed, wherein a condensed portion of the overhead gas is used partially or completely as a reflux in the rectification and an uncondensed portion of the overhead gas is provided partially or completely as the third gas fraction (G3).

3. Process according to claim 2, in which the rectification is carried out using a rectification column (T2), the condensed proportion of the overhead gas or its portion being fed back to the rectification column (T2) without using a reflux pump and/or a reflux vessel arranged outside the column.

4. Process according to claim 1, in which the first temperature level is 0 to 50° C., the second temperature level is −30 to −40° C. and the third temperature level is −50 to −60° C.

5. Process according to claim 1, in which the third liquid fraction is formed in the rectification at a temperature level of 65 to 75° C.

6. Process according to claim 2, in which rectification is accomplished using a rectification column (D2) which is cooled with a tops condenser which is operated with propane and/or propylene coolant.

7. Process according to claim 1, in which a fraction containing more than 95% hydrogen and methane and a fraction containing more than 95% hydrocarbons having two carbon atoms are formed from at least a portion of the second gas fraction (G4) and the third gas fraction (G3) in a further separation apparatus (S1).

8. Process according to claim 7, in which the further separation apparatus (S1) is operated at the second pressure level.

9. Process according to claim 7, in which at least a portion of the second gas fraction (G4) is subjected to further partial condensations by means of stepwise cooling via one or more intermediate temperature levels to a fourth temperature level at the first pressure level to obtain further liquid fractions (C3, C4, C5).

10. Process according to claim 9, in which the further liquid fractions are fed into the separation apparatus (S1).

11. Process according to claim 9, in which a proportion (G9) of the second gas fraction (G4) that remains in gaseous form at the fourth temperature level is expanded from the first pressure level to the second pressure level to provide refrigeration energy and fed into the further separation apparatus (S1).

12. Process according to claim 9, in which the fourth temperature level is −140 to −150° C.

13. Process according to claim 9, in which the fraction containing more than 95% hydrogen and methane is taken from the further separation apparatus (S1), expanded from the second pressure level to a third pressure level to provide refrigeration energy, and used for stepwise cooling to the fourth temperature level.

14. Process according to claim 7, in which the separation apparatus (S1) is operated with an internal heat exchanger which is cooled with a coolant at a temperature level of −90 to −110° C.

15. Plant (100, 200) for separation of a component mixture (K) comprising hydrogen, methane, hydrocarbons having two carbon atoms and hydrocarbons having three or more carbon atoms, wherein the plant (100, 200) comprises means for deethanization and means for demethanization, wherein the demethanization is subsequent to the deethanization, and wherein the means for deethanization comprise a first heat exchanger (E1) and a first vessel (D1) which are set up to subject at least a portion of the component mixture (K) to a first partial condensation by cooling from a first temperature level to a second temperature level at a first pressure level to obtain a first gas fraction (G1) and a first liquid fraction (C1), the means for deethanization comprise a second heat exchanger (E2) and a second vessel (D2) which are set up to subject at least a portion of the first gas fraction (G1) to a second partial condensation by cooling from the second temperature level to a third temperature level at the first pressure level to obtain a second gas fraction (G4) and a second liquid fraction (C2), the means for deethanization comprise a deethanization column (T2) which is set up to subject at least a portion of the first liquid fraction (C1) and at least a portion of the second liquid fraction (C2) to a rectification to obtain a third gas fraction (G3) and a third liquid fraction (C3+), the second heat exchanger (E2) and the second vessel (D2) which are provided as means for the second partial condensation are set up to perform the second partial condensation such that the second gas fraction (G4) comprises more than 95% hydrogen, methane and hydrocarbons having two carbon atoms, and means are provided in the form of expansion valves which are arranged to expand the first liquid fraction (C1) or its part subjected to the rectification and the second liquid fraction (C2) or its part subjected to the rectification from the first pressure level to a second pressure level before the rectification and to carry out the rectification at the second pressure level, the first pressure level being 25 to 35 bar and the second pressure level being 14 to 17 bar, characterized in that means are provided in the form of a head condenser (E7) mounted on top of the deethanization column (T2) which are adapted to cool an overhead gas formed during rectification to −25 to −35° C. and thereby partially condense it, and to use a condensed portion of the overhead gas partially or completely as a reflux in the rectification and to provide a non-condensed portion of the overhead gas partially or completely as the third gas fraction (G3).

* * * * *